United States Patent [19]

Zimmermann

[11] 4,420,559

[45] Dec. 13, 1983

[54] METHOD OF ENZYMATICALLY CONVERTING A SUBSTRATE USING MEMBRANE VESICLES

[75] Inventor: Ulrich Zimmermann, Jülich, Fed. Rep. of Germany

[73] Assignee: Kernforschungsanlage Jülich Gesellschaft mit beschränkter Haftung, Jülich, Fed. Rep. of Germany

[21] Appl. No.: 448,721

[22] Filed: Dec. 10, 1982

Related U.S. Application Data

[63] Continuation-in-part of Ser. No. 248,318, Mar. 27, 1981, abandoned, which is a continuation of Ser. No. 61,517, Jul. 27, 1979, abandoned, which is a continuation of Ser. No. 871,217, Jan. 23, 1978, abandoned, which is a continuation-in-part of Ser. No. 688,918, May 21, 1976, abandoned, which is a continuation-in-part of Ser. No. 472,472, May 22, 1974, abandoned.

[30] Foreign Application Priority Data

May 23, 1973 [DE] Fed. Rep. of Germany ....... 2326161

[51] Int. Cl.$^3$ .............................................. C12P 19/14
[52] U.S. Cl. ....................................... 435/99; 435/41; 435/168; 435/174; 435/177
[58] Field of Search ................... 435/94, 262, 99, 168, 435/41, 174, 177

[56] References Cited

U.S. PATENT DOCUMENTS

| Re. 29,130 | 1/1977 | Lee et al. | 435/94 |
| 3,935,068 | 1/1976 | Nystrom | 435/94 |
| 4,001,082 | 1/1977 | Tsumura | 435/94 |
| 4,033,817 | 7/1977 | Gregor | 435/94 X |
| 4,060,456 | 11/1977 | Long | 435/94 |

OTHER PUBLICATIONS

Kaback "Methods of Enzymology" vol. XXII Enzymes Purification & Related Techniques Chapter 13 Bacterial Membranes Academic Press 1971, pp. 99–121.

*Primary Examiner*—R. B. Penland
*Attorney, Agent, or Firm*—Becker & Becker, Inc.

[57] ABSTRACT

The present invention relates to a method involving enzymatic catalyzed chemical reactions with substrates dissolved in an aqueous solution by means of enzymes. Membrane vesicles, loaded with the enzymes, are placed into the aqueous solution. The substrates move into the membrane vesicles where they are decomposed by means of the enzymes trapped in the vesicles. The substances produced by decomposition move out of the vesicles into the aqueous solution. Finally the decomposed substances are separated from the aqueous solution.

5 Claims, No Drawings

METHOD OF ENZYMATICALLY CONVERTING A SUBSTRATE USING MEMBRANE VESICLES

RELATED APPLICATIONS

This is a continuation-in-part of co-pending application Ser. No. 248,318-Zimmermann, filed Mar. 27, 1981, now abandoned which was a continuation of Ser. No. 061,517-Zimmermann, filed July 27, 1979, now abandoned, which is a continuation of Ser. No. 871,217-Zimmermann, filed Jan. 23, 1978, now abandoned, which is a continuation-in-part of Ser. No. 688,918-Zimmermann, filed May 21, 1976, now abandoned, which in turn is a continuation-in-part of parent application Ser. No. 472,472-Zimmermann, filed May 22, 1974, now abandoned.

BACKGROUND OF THE INVENTION

(1) Field of the Invention

The present invention relates to a method for enzymatic catalyzed reactions by exposing a substrate in an aqueous solution to an enzyme, the aqueous solution containing at least 0.5 mM/1 magnesium and/or calcium and potassium ions.

(2) Technical Considerations and Prior Art

The purpose of these steps consists in producing biochemical and pharmaceutical products in an economical manner as it occurs, for instance, when decomposing cane sugar to glucose and fructose. Moreover, the decomposition of toxic acting substances is intended, for instance, the decomposition of urea in the blood to carbon dioxide and ammonium.

It is known to use the catalytic action of enzymes for building up and decomposing substances. Thus, for instance, it has been suggested to adsorb enzymes on inorganic or organic carriers and to make them effective in this way. It is also known to include enzymes for composing or decomposing substances in pores of a gel. Finally, the state of the art also includes the binding of enzymes to a reaction capable polymer matrix for composing or decomposing substances. All of these known methods, however, have the great disadvantage that the degree of efficiency of the enzymes was relatively low so that the output in substances to be composed or decomposed was so low that these methods were not economical enough for practical use.

SUMMARY OF THE INVENTION

It is therefore an object of the present invention to provide a method for decomposing substances dissolved in aqueous solutions, by the use of enzymes; a method, which is practicable in an economical manner and will within a relatively short time assure a satisfactory output.

This object has been realized by the method according to the present invention, which is characterized primarily by the provision of membrane vesicles which are formed out of erythrocytes. These erythrocytes have a content and osmolarity value which are known. The erythrocytes are placed in a first aqueous solution containing enzymes and having an osmolarity which is less than that of the erythrocytes. The osmolarity of the solution when compared with the osmolarity of the erythrocytes content has to be so low that a permeability increase of the membranes of the erythrocytes is thereby effected. This causes the cell periphery to act as a diaphragm which is porous enough that the enzymes migrate into the erythrocytes while the erythrocytes' contents flow out. The erythrocytes are left in the first solution containing the enzymes until, as a consequence of material interchange or osmosis through the cell skin which is effective as a membrane and now provides an increase in permeability, there is obtained an equilibrium condition between the solution containing the cell interior and the solution containing the enzymes so that, in effect, the original content of the erythrocytes is replaced by the solution containing the enzymes. Subsequently thereto, the osmolarity of the solution containing the enzymes is increased to its original value by way of addition of at least one osmotically active material such as calcium ions, potassium ions, sodium ions, etc. so as to become equal to the osmolarity of the cell content of the originally introduced erythrocytes. The osmotically active material, however, must be compatible with the cell membrane so as to stabilize it.

Thereupon after formation of the loaded membrane vesicles according to the aforementioned method steps, the vesicles are separated from the solution containing the enzymes.

The loaded vesicles are placed in an (second) aqueous solution which contains the substrate or material which is to be reacted. The vesicle periphery is sufficiently permeable that the substrate moves into the interior of the vesicle and reacts with the enzyme contained therein. The products which are created by decomposition move out of the vesicle into the aqueous solution and may be separated, in a manner known per se, from the aqueous solution.

The method according to the invention is based on the finding that the cell skin becomes more permeable when cells are introduced into a solution with an osmolarity which is lower that the cell content. The method is furthermore based on the finding that the cell skin becomes non-permeable for enzymes moved into the interior of the cell when the cell skin has reached its original permeability.

Notation is made for the production of membrane vesicles that, aside from cells which occur as single cells in a physiological solution, as for example erythrocytes, also such cells are usable which are arranged in an interwoven manner, in other words, arranged with cells connected in conjunction with each other. The cell binding or connection of a weave or composition can, as is familiar to every man skilled in the art, be dissolved by way of biochemical or biophysical manner so that suspendable cells are received in a solution. A characteristic pertinent to all living cells of living things particularly is that the permeability of the cell membrane (or cell skin) can be increased by means of the influence or the effectiveness of osmotic forces. Furthermore, the permeability increase is capable of being healed so that the cell again receives the original permeability thereof.

During the carrying out of the method, however, one fact that has to be taken into account is that there are subspendable cells of living things of which the cell membrane is surrounded by a cell wall which supports the membrane. It is not possible with all cells to produce membrane vesicles according to the method of the present invention without previously removing the cell wall. In such cases, for instance with bacteria cells, the cell wall must previously be removed as mentioned earlier in this description. With "Dunaliella" algae which have a type of cell wall, it is not necessary to remove the cell wall before carrying out the method according to the present invention. This is apparent from a sample embodiment set forth subsequently herein.

It is noted that after accomplishing permeability reduction of the cell membrane the loaded membrane vesicles are produced. The cell content now for all practical purposes consists of a solution which contains enzymes and of which the osmolarity corresponds within limits to the osmolarity of the aqueous solution. Thus, since the cell plasma has been interchanged with enzymes a cell is no longer involved in the process; the original cell has now become a loaded membrane vesicle. The membrane vesicles accordingly are separated from the solution containing enzymes. This can be realized by flotation, sedimentation, filtration, or centrifuging. The vesicles purposely are given or introduced into a physiological solution since naturally only therein they are capable of living.

Since the loaded membrane vesicles are provided for reaction of the enzymes with substrate materials in an aqueous solution each of the original cells must have an osmolarity which diverges only within limits from the osmolarity of the aqueous solution. It is noted that the osmolarity of the content of the loaded membrane vesicles corresponds to the osmolarity of the original cell content.

Since the aqueous solution must be a physiological solution, in which only the cells are capable of living, it is noted that the aqueous solution must contain at least 0.5 mM/1 magnesium ions and/or calcium ions, as well as potassium ions.

The concentration of the entirety of the osmotically active materials in the aqueous solution containing the substrate may differ from case to case however. This will depend upon the type of cell which is utilized, the desired reaction, etc.

Advantageously the first solution has an osmolarity which is less that 70% of the osmolarity of the content of the erythrocytes.

The first solution contains osmotically active substances at least half of the substances in the first solution being cell skin stabilizing ions selected from the group consisting of magnesium ions, calcium ions, and potassium ions.

Advantageously the erythrocytes are left in the (first) aqueous solution containing the enzymes at a temperature of 0° C. until osmotic equilibrium is reached and further the osmotically active substances are added to the first solution (containing the enzymes) maintained at a temperature of 37° C.

The method steps for utilization of the produced membrane vesicles for reacting with materials dissolved in the (second) aqueous solution including at least 0.5 mM/1 magnesium ions and/or calcium ions, as well as potassium ions, can be summarized by the following:

the membrane vesicles are inserted into the aqueous solution until the materials to be reacted wander into the inside of the membrane vesicles as a result of the permeability of the membrane vesicles and until the reaction of the materials is terminated and the reaction products have migrated through the membrane into the aqueous solution; and in sequence thereupon the reaction products are separated from the aqueous solution.

Preferably the (second) aqueous solution has an osmolarity which is only as much as 20% less than the osmolarity of the content of the loaded membrane vesicles.

The method of the present invention makes it possible for the first time, to realize, for instance, the decomposition of the cane sugar to glucose and fructose by means of the enzyme Invertase without the said enzyme being dissolved in the cane sugar solution or without said enzyme losing its catalytic activity.

SAMPLE EMBODIMENT 1

Erythrocytes were introduced into a Tris solution with a pH-value of 7.2 while a suspension density of 40 g% of the erythrocytes were adjusted in the solution. Added to 50 ml of this solution were 500 ml of a solution which contained 5 mM/1 $MgSO_4$ and 1 mg% Invertase. The thus produced solution was kept for 30 minutes at a temperature of approximately 0° C. Subsequently thereto, the osmolarity of the solution was set to the osmolarity of the original Tris solution, while a suitable quantity of solution containing 155 mM/1 NaCl was added. At the same time, the temperature of the solution was increased to 37° C., and this temperature was maintained for approximately 50 minutes. The membrane vesicles containing the enzyme Invertase were than separated by centrifuging in a centrifuge at 30,000 gram.

The centrifuged membrane vesicles were then added to 100 ml of an isotone Tris solution with a pH-value of 7.5 which contained $10^{-3}$ mol/1 cane sugar. After the loaded membrane vesicles were left for approximately 30 minutes in the solution containing the converting raw sugar, they were separated by being centrifuged off. A determination of the cane sugar concentration in the remaining solution indicated a 90% conversion of the raw sugar to glucose and fructose. Since previously known methods have yielded a conversion of from 1% to 50%, this represents a considerable improvement over known methods.

SAMPLE EMBODIMENT 2

Erythrocytes were washed twice in an isotone, phosphate buffered sodium chloride solution and were then taken out by way of centrifuging. The solution contained 138 mM/1 sodium chlorides, 12.3 mM/1 Dinatriumhydrogen phosphate. The pH-value of the solution amounts to 7.4.

The washed erythrocytes were given in a ratio of one volume part erythrocytes to one volume part of the aforementioned sodium chloride solution. The so formed solution containing the erythrocytes was introduced while stirring it at 0° C. in a volume ratio or relationship of 1:10 into a solution of 4 mM/1 magnesium sulphate which additionally contained 5 mg/100 ml Urease. After five minutes, the osmolarity of the solution now containing the erythrocytes was elevated or increased to attaining the isotonitate by way of addition of two molarer potassium chloride solution. After a further five minutes the temperature was increased for approximately thirty minutes to 37° C. Subsequent thereto, the so formed membrane vesicles which contain the enzyme Urease were washed by way of five times centrifuging them out of isotone, phosphate buffered sodium chloride solution of the aforementioned composition in order to remove possible Urease bonding on the outer upper surface of the membrane vesicles.

The membrane vesicles containing the Urease were subsequently utilized for building up urea material by incubating them in an isotone, phosphate buffered sodium chloride solution of the aforementioned composition which contained 20 mM/l of urea material. In predetermined time intervals, the ammonia ions formed by way of splitting of the urea material were determined photometrically according to the method of Berthelot reaction whereby for this purpose a part of the solution was utilized from which the membranes previously were separated. The measurements resulted in an activity of the Urease enclosed or encapsulated in the cells amounting to 0.4 micromol urea material per minute and per ml membrane vesicles.

As a control, erythrocytes were treated according to the aforementioned described method for production of membrane vesicles without, however, the enzyme Urease being introduced into the solution providing a lower osmolarity. Accordingly, membrane vesicles were formed without thereby, however, enclosing or encapsulating an enzyme. After healing of permeability increase, in other words, after production of the enzymeless membrane vesicles, these were introduced for several minutes into a solution containing Urease. Subsequently, the membrane vesicles were washed in the aforementioned manner by way of five times centrifuging them out of a sodium chloride solution. The method steps carried out subsequently in the aforementioned manner for utilization of the membrane vesicles resulted in no formation of ammonia ions. In this manner, it was assured that the formation of the ammonia ions in the aforementioned sample embodiment were not dissolved or released by way of Urease bonding on the upper surface of the membrane vesicles.

SAMPLE EMBODIMENT 3

Proceding from erythrocytes there were produced membrane vesicles in the same manner as with the sample embodiment 2 whereby, however, in place of the enzyme Urease, the enzyme glucoseoxidase was introduced into the solution containing 4 mM/l magnesium sulphate.

The glucose-oxidase containing membrane vesicles were utilized subsequently for building up glucon acid in incubating the vesicles in a phosphate buffered sodium chloride solution, while gasifying the solution with air, the solution having a composition equal to the solution of sample embodiment 2 but additionally containing 20 mM/l glucose. The glucon acid formed out of glucose and oxygen was determined with the method of thin-layer-chromathography. As with the sample embodiment 2 there was utilized a part of the solution out of which the membrane vesicles had been separated.

Control investigations resulted therein that no glucon acid was effected by way of glucose-oxidase bonding on the upper surface of the membrane vesicles.

SAMPLE EMBODIMENT 4

As cells there are used Dunaliella algae which were cultured in a solution containing the subsequently listed material quantities:

1.5 M/l sodium chloride (NaCl); 24 mM/l magnesium sulphate ($MgSO_4$); 20 mM/l magnesium chloride ($MgCl_2$); 10 mM/l calcium chloride ($CaCl_2$); 4 mM/l sodium nitrate ($NaNO_3$); 1 mM/l potassium nitrate ($KNO_3$); 0.1 mM/l potassium hydro phosphate ($K_2HPO_4$); 1.5 Micromol/l iron chloride ($FeCl_3$); 30 Micromol/l (EDTA); 185 Micromol ($H_3BO_3$); 7 Micromol manganese chloride ($MnCl_2$); 0.8 Micromol/l zinc chloride ($ZnCl_2$); 0.02 Micromol/l cobalt chloride ($CoCl_2$); 0.2 Micromol/l copper chloride ($CuCl_2$); and 20 mM/l trisulphide chloride (Tris-Cl).

After centrifuging off from the aforementioned growth medium the algae were suspended in a weight 1:1 with a medium having the following composition:

1.5 M/l sodium chloride (NaCl); 10 mM/l magnesium chloride ($MgCl_2$); 21.3 mM/l potassium hydro phosphate ($KH_2PO_4$); 3.7 mM/l sodium hydro phosphate ($Na_2HPO_4$). The pH-value of this solution was 7.5.

Subsequently 1 ml of the so-formed suspension was introduced for formation of enzyme loaded membrane vesicles into 10 ml of a 0.45 M/l sodium chloride solution which contained 0.5 mg Urease. The temperature of the solution amounted to 15° C. After thirty minutes, the original osmolarity was again achieved by adding a corresponding quantity of a 3 M/l sodium chloride solution and the algae was left in the solution for a further thirty minutes at 15° C.

Subsequent thereto, the cells were washed after centrifuging five times in medium utilized for formation of the suspension in order to possibly remove Urease bonding therewith.

The membrane vesicles containing the Urease were used subsequently thereto for tearing down or breaking down the urea material by incubating the vesicles into the medium used for washing relative to which additionally 20 mM/l urea material was added. In predetermined time intervals, the ammonia ions formed by splitting of the urea material were determined photometrically according to the method by Berthelot reaction. The measurements resulted in an activity of the Urease enclosed in the membrane vesicles of 0.03 Micromol urea material per minute and per ml membrane vesicles.

This value resulted after deducting the natural urea activity of a suspension formed for control, which was produced corresponding to the control investigation set forth in the sample embodiment 2.

The present invention is, of course, in no way restricted to the specific disclosure of the specification, but also encompasses any modifications within the scope of the appended claims.

What I claim is:

1. A method for enzymatically converting a substrate in an aqueous solution using an enzyme entrapped in membrane vesicles and suspended in the solution, the method comprising the steps of:

suspending erythrocytes in a first aqueous solution having an osmolarity which is less than 70% of the content of the erythrocytes said solution containing at least 0.5 mM/l of ions selected from the group consisting of magnesium, calcium and potassium ions; and low enough to increase the permeability of the membrane of the erythrocytes;

leaving said erythrocytes in said first aqueous solution until osmotic equilibrium is reached between the contents of said erythrocytes and said first solution, thereby producing membrane vesicles from said erythrocytes and loading said membrane vesicles with an enzyme;

adding to said first solution containing said enzyme loaded membrane vesicles osmotically active substances selected from the group consisting of calcium, potassium, and sodium ions to increase the osmolarity of the first solution thereby reducing said permeability of the membrane of the membrane vesicles entrapping the enzymes therein;

separating said loaded membrane vesicles from said first aqueous solution;

suspending said loaded membrane vesicles in a second aqueous solution having an osmolarity up to 20% less than the osmolarity of said loaded membrane vesicle, said second aqueous solution containing the substrate to be degraded;

holding said loaded membrane vesicles in said second aqueous solution for a period of time sufficient to allow the substrate to enter said membrane vesicles and be degraded by said enzyme and to produce reaction products which reaction products leave said membrane vesicles and accumulate in said second aqueous solution; and separating said loaded membrane vesicles from said reaction products.

2. A method as claimed in claim 1, in which said erythrocytes are left in said first solution at a temperature of 0° C. until said osmotic equilibrium is reached.

3. A method as claimed in claim 1, in which said osmotically active substances are added to said first solution which is maintained at a temperature of 37° C.

4. The method of claim 1, in which the enzyme is Invertase and the substrate in the said aqueous solution is cane sugar and wherein the reaction products are glucose and fructose.

5. The method of claim 1, in which the enzyme is Urease and the substrate in the said aqueous solution is urea material and wherein the reaction products are ammonia ions.

* * * * *